United States Patent
Saruwatari et al.

(10) Patent No.: US 6,943,273 B2
(45) Date of Patent: *Sep. 13, 2005

(54) METHOD FOR PRODUCING BISPHENOL-A

(75) Inventors: Tetsuya Saruwatari, Yamaguchi (JP); Masahiro Iwahara, Yamaguchi (JP)

(73) Assignee: Idemitsu Kosan Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/433,155

(22) PCT Filed: Aug. 2, 2002

(86) PCT No.: PCT/JP02/07924
§ 371 (c)(1),
(2), (4) Date: May 30, 2003

(87) PCT Pub. No.: WO03/014049
PCT Pub. Date: Feb. 20, 2003

(65) Prior Publication Data
US 2004/0030196 A1 Feb. 12, 2004

(30) Foreign Application Priority Data
Aug. 6, 2001 (JP) ........................................ 2001-237889

(51) Int. Cl.$^7$ ............................................. C07C 39/16
(52) U.S. Cl. ...................................................... 568/728
(58) Field of Search ......................................... 568/728

(56) References Cited

U.S. PATENT DOCUMENTS

| | | | |
|---|---|---|---|
| 4,308,404 A | | 12/1981 | Kwantes et al. |
| 4,400,555 A | * | 8/1983 | Mendiratta ................... 568/728 |
| 5,777,180 A | * | 7/1998 | June et al. ................... 568/728 |
| 6,414,199 B1 | | 7/2002 | Saruwatari |
| 6,429,343 B1 | * | 8/2002 | Iwahara ...................... 568/728 |
| 6,608,234 B2 | | 8/2003 | Saruwatari |
| 6,740,784 B2 | * | 5/2004 | Iwahara et al. ............. 568/728 |

FOREIGN PATENT DOCUMENTS

| | | | |
|---|---|---|---|
| EP | 0 567 857 | 11/1993 | |
| EP | 1 160 229 | 12/2001 | |
| EP | 1 371 623 | 12/2003 | |
| JP | 6-92889 | 4/1994 | |
| JP | 8-40961 | 2/1996 | |
| JP | 11-246458 | 9/1999 | |
| WO | 00/61532 | 10/2000 | |
| WO | WO 01/49640 | * 7/2001 | ............ B01J/31/08 |

OTHER PUBLICATIONS

U.S. Appl. No. 10/433,155, filed May 30, 2003, Saruwatari et al.*
U.S. Appl. No. 10/468,152, filed Aug. 27, 2003, Iwahara et al.*
U.S. Appl. No. 10/204,264, filed Aug. 20, 2002, Saruwatari.
U.S. Appl. No. 10/257,980, filed Oct. 29, 2002, Saruwatari et al.
U.S. Appl. No. 10/258,571, filed Oct. 30, 2002, Saruwatari.
U.S. Appl. No. 10/433,155, filed May 30, 2003, Iwahara et al.
U.S. Appl. No. 10/458,192, filed Jun. 11, 2003, Saruwatari.

* cited by examiner

*Primary Examiner*—Michael L. Shippen
(74) *Attorney, Agent, or Firm*—Oblon, Spivak, McClelland, Maier & Neustadt, P.C.

(57) ABSTRACT

Provided is a process for producing a bisphenol A by continuously feeding phenol and acetone into a reactor unit having at least two reaction zones connected in series. In the process, an acidic cation-exchange resin partially neutralized with a sulfur-containing nitrogen compound in from 15 to 50% of the acid site thereof is used as the catalyst, and acetone having a methanol concentration of at most 3,000 ppm is separately fed into at least two reaction zones in the reactor unit. The life of the acidic cation-exchange resin catalyst used in the process is prolonged.

20 Claims, 1 Drawing Sheet

METHOD FOR PRODUCING BISPHENOL-A

TECHNICAL FIELD

The present invention relates to a process for producing bisphenol A in which the life of the catalyst, acidic cation-exchange resin used can be prolonged. Bisphenol A is useful as a material for polycarbonate resin, epoxy resin, polyarylate resin, etc.

BACKGROUND ART

Bisphenol A [2,2-bis(4-hydroxyphenyl)propane] is known to be an important compound for a material for engineering plastics such as polycarbonate resin and polyarylate resin or for epoxy resin, and there is increasing a great demand for it these days.

It is known that bisphenol A is produced by condensing acetone and excess phenol in the presence of an acidic cation-exchange resin catalyst and optionally a sulfur compound promoter such as alkylmercaptan. In the process, the acidic cation-exchange resin catalyst degrades with time. A principal cause of the catalyst degradation is the heavy material derived from the starting compounds, and the catalyst begins to degrade first around the inlet port of the reactor. Since its degradation speed is high, an excess amount of the catalyst is charged into the reactor for long-term continuous operation for bisphenol A production. After the catalyst has begun to degrade, the amount of acetone to be fed into the reactor must be time-dependently increased for keeping the product yield (that is, for keeping the intended degree of phenol conversion). In that case, the non-reacted acetone that goes out of the reactor is recovered in the distillation column connected to the outlet port of the reactor. Therefore, the amount of acetone that maybe increased in the process is limited by the capacity of the distillation column. That is, at the limit of the capacity of the distillation column, the catalyst in the reactor is exchanged with a fresh one. Accordingly, if the reaction condition could be suitably controlled so as not to increase the amount of acetone and so as to use the catalyst as long as possible in the reactor, it will reduce the production costs. In this connection, some patent applications relating to improvement of the reaction condition have been laid open to public inspection, though their objects differ. For example, Japanese Patent Laid-Open No. 19952/1979, Japanese Patent No. 2,779,952, Japanese Patent Laid-Open No. 246458/1999 and U.S. Pat. No. 4,400,555 disclose a specific arrangement of reactors connected in series in which a carbonyl compound divided into some portions is added separately to each reactor. In these, however, there is still room for improvement for prolonging the life of the acidic cation-exchange resin used.

The present invention has been made in consideration of the above-mentioned matters, and its object is to provide a process for producing bisphenol A in which the life of the catalyst, acidic cation-exchange resin used can be prolonged.

DISCLOSURE OF THE INVENTION

We, the present inventors have assiduously studied, and, as a result, have found that, in a process of producing bisphenol A by continuously feeding phenol and acetone into a reactor unit having at least two reaction zones connected in series, when an acidic cation-exchange resin that has been specifically partially neutralized is used as the catalyst and when acetone having a specific methanol concentration is separately fed into at least two reaction zones in the reactor unit, then the process ensures a high degree of phenol conversion. On the basis of this finding, we have completed the present invention.

Specifically, the invention provides a process for producing a bisphenol A by continuously feeding phenol and acetone into a reactor unit having at least two reaction zones connected in series, which is characterized in that an acidic cation-exchange resin partially neutralized with a sulfur-containing nitrogen compound in from 15 to 50% of the acid site thereof is used as the catalyst, and acetone having a methanol concentration of at most 3,000 ppm is separately fed into at least two reaction zones in the reactor unit.

BEST MODES OF CARRYING OUT THE INVENTION

Figure 1:
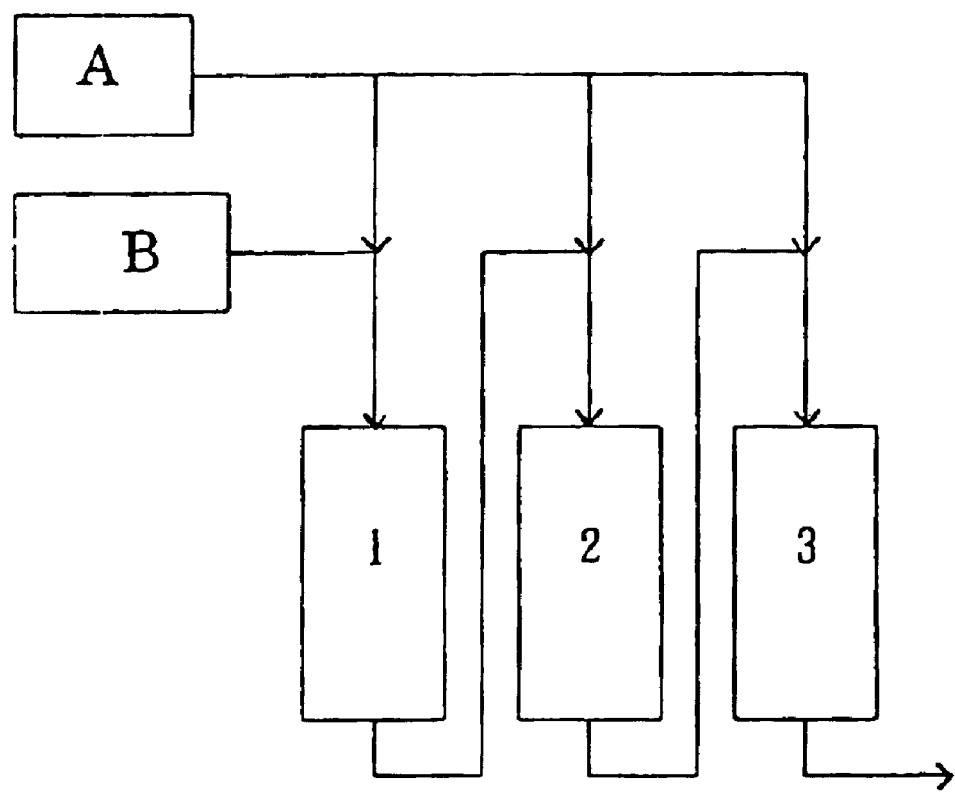
FIG. 1 shows one example of a flowchart of reaction steps of the process of the invention. A indicates acetone; B indicates phenol; 1 indicates a first reactor; 2 indicates a second reactor; and 3 indicates a third reactor.

The invention is described in detail hereinunder.

First described is the outline of the steps of the process for producing bisphenol A of the invention.

Step (1) (Reaction Step)

Bisphenol A is produced by reacting acetone with excess phenol in the presence of an acidic cation-exchange resin catalyst and optionally an alkylmercaptan serving as a promoter. For the acidic cation-exchange resin catalyst, generally preferred is a sulfonic acid-type cation-exchange resin. For example, it includes sulfonated styrene-divinylbenzene copolymer, sulfonated crosslinked styrene polymer, phenol-formaldehyde-sulfonic acid resin, and benzene-formaldehyde-sulfonic acid resin. Singly or as combined, one or more of these may be used as the catalyst.

In addition to the product bisphenol A therein, the reaction mixture contains non-reacted phenol, non-reacted acetone, catalyst, by-produced water, alkylmercaptan, as well as side products such as organic sulfur compounds and color substances.

Step (2) (Step of Recovering By-produced Water and Non-reacted Compounds)

Next, the reaction mixture obtained in the step (1) is distilled under reduced pressure, whereby the non-reacted acetone, by-produced water and alkylmercaptan are removed through the top of the distillation column and a liquid mixture that contains bisphenol A and phenol is taken out through the bottom thereof. The condition for the reduced-pressure distillation in this step is as follows: The pressure falls between 7 and 80 kPa, and the temperature falls between 70 and 180° C. In that condition, the non-reacted phenol forms an azeotrope and a part of it is removed out of the system through the top of the distillation column.

Step (3) (Step of Condensing Bisphenol A)

The bottom liquid of the reaction mixture from which the substances as above have been removed is then distilled under reduced pressure to remove phenol from it, and the product bisphenol A is thereby condensed. The resulting condensate residue is crystallized in the next step. The condensation condition is not specifically defined. In general, the temperature falls between 100 and 170° C., and the pressure falls between 5 and 67 kPa. If the temperature is lower than 100° C., the condensation will require high vacuum; but if higher than 170° C., the next crystallization step will require an additional treatment for heat removal. The bisphenol A concentration of the condensate residue may fall between 20 and 50% by mass, but preferably between 20 and 40% by mass. If the concentration is lower than 20% by mass, the bisphenol A recovery will be low; but if higher than 50% by mass, the slurry transfer after crystallization will be difficult.

Step (4) (Crystallization Step)

The condensate residue obtained in the step (3) is cooled to 40 to 70° C. to give a crystal of bisphenol A-phenol adduct (hereinafter this is abbreviated as phenol adduct), and it becomes slurry. Cooling the residue may be effected by applying water to the external heat exchanger or crystallizer fitted to the reactor unit for heat removal from the residue through vaporization of water. Next, the condensate residue slurry is filtered or centrifuged to separate the phenol adduct from the crystal-free mother liquid that contains side products. The mother liquid is directly or partly recycled into the reactor unit, or apart or all of it is decomposed with alkali into phenol and isopropenylphenol and they are recovered. As the case may be, a part or all of the mother liquid may be isomerized and recycled to crystallization.

Step (5) (Step of Heating and Melting Phenol Adduct)

The crystal of 1:1 adduct of bisphenol A and phenol obtained in the step (4) is melted under heat at 100 to 160° C. into a liquid mixture.

Step (6) (Step of Recovering Bisphenol A)

Through distillation under reduced pressure, phenol is removed from the liquid mixture obtained in the step (5), and bisphenol A is thus recovered. The condition of the reduced-pressure distillation is as follows: The pressure falls between 1 and 14 kPa; and the temperature falls between 150 and 190° C. Apart from such treatment, another method of removing the remaining phenol through steam stripping is also known.

Step (7) (Step of Granulating Bisphenol A)

The bisphenol A obtained in melt in the step (6) is formed into liquid drops in a granulator such as spray drier, then cooled and solidified. This is the final product of the invention. The liquid drops are formed by spraying or sprinkling the melt and then cooled by exposing them to nitrogen or air.

Next, the process of the invention is described in detail.

The process of the invention is for producing bisphenol A by continuously feeding phenol and acetone into a reactor unit having at least two reaction zones connected in series, and is characterized in that an acidic cation-exchange resin partially neutralized with a sulfur-containing nitrogen compound in from 15 to 50% of the acid site thereof is used as the catalyst, and acetone having a methanol concentration of at most 3,000 ppm is separately fed into at least two reaction zones in the reactor unit.

Specifically in the process the catalyst to be used is an acidic cation-exchange resin partially neutralized with a sulfur-containing nitrogen compound in from 15 to 50% of the acid site thereof. If the degree of neutralization of the cation-exchange resin used as the catalyst in the process is lower than 15%, the catalyst will lose the methanol resistance of itself and the separate addition of acetone to different reactors will be ineffective. If higher than 50%, on the other hand, it is unfavorable since the catalyst activity greatly lowers. Preferably, the degree of neutralization of the catalyst falls between 20 and 30%.

The sulfur-containing nitrogen compound to be used for the catalyst neutralization includes, for example, pyridinealkanethiols such as 3-mercaptomethylpyridine, 3-mercaptoethylpyridine, 2-mercaptoethylpyridine, 4-mercaptoethylpyridine; pyridylalkanethioacetals to be obtained from such pyridinealkanethiols with ketones such as acetone, methyl ethyl ketone, methyl isobutyl ketone, acetophenone, cyclohexanone; aminoalkanethiols such as 2-mercaptoethylamine, 3-mercaptobutylamine, 3-n-propylamino-1-propylmercaptan; and thiazolidines such as thiazolidine, 2,2-dimethylthiazolidine, cycloalkylthiazolidines. Above all, preferred are 2,2-dimethylthiazolidine and 2-mercaptoethylamine.

In the process, it is also indispensable that the methanol concentration of acetone is at most 3,000 ppm. If higher than 3,000 ppm, it is unfavorable since the influence of methanol on the process is too great. Preferably, the methanol concentration is at most 2,000 ppm.

The reaction temperature preferably falls between 60 and 100° C. If lower than 60° C., it is unfavorable since the phenol phase will solidify; but if higher than 100° C., it is also unfavorable since the ion-exchange resin used will be too much degraded. More preferably, the reaction temperature falls between 65 ad 95° C.

Also preferably, the ratio (by mol) of phenol/total acetone falls between 6 and 13. If smaller than 6, it is unfavorable since the color of the product, bisphenol A will be unstable; but if higher than 13, it is also unfavorable since the reaction speed will be low and the amount of phenol to be recovered will increase. More preferably, the ratio falls between 8 and 12.

The amount of acetone to be fed into each reactor is not specifically defined. For example, from 30 to 50% of all acetone to be fed into the reactor unit may be fed into the first reactor, and the remaining acetone is divided into equal parts and equally fed into the second and later reactors. FIG. 1 is a flowchart showing one example of the invention that uses a three-stage reactor unit.

Preferably, the liquid hourly space velocity (LHSV) in each reactor falls between 0.2 and 30 $hr^{-1}$, more preferably between 0.5 and 6 $hr^{-1}$.

The invention is described more concretely with reference to the following Examples, which, however, are not intended to restrict the scope of the invention.

EXAMPLE 1

69 cc of an acidic cation-exchange resin neutralized with 2,2-dimethylthiazolidine in 20% of the acid site thereof (Mitsubishi Chemical's Diaion SK104) was, after swollen with water, charged into each of three stainless columns. 277 cc/hr of phenol and 8 cc/hr of acetone were fed into the reactor unit through the inlet port of each reactor column. The reaction temperature in the unit was kept at 75° C. The ratio (by mol) of phenol/all acetone was 10. The methanol concentration of the acetone was 1,000 ppm. In the initial stage of reaction, the phenol conversion at the outlet port of the third reactor column was 14.0%, and after 500 hours, it was 12.8%.

COMPARATIVE EXAMPLE 1

In the same reactor unit as in Example 1, all acetone was fed into the first reactor column at a flow rate of 24 cc/hr, and reacted with phenol in the same manner as in Example 1. In the initial stage of reaction, the phenol conversion at the outlet port of the third reactor column was 14.0%, but after 500 hours, it was 12.0%. There is a significant difference between the data, 12.8% in Example 1 and 12.0% in Comparative Example 1.

COMPARATIVE EXAMPLE 2

In the same reactor unit as in Example 1, an ion-exchange resin having a degree of neutralization of 10% was used and acetone and phenol were reacted in the same manner as in Example 1. In the initial stage of reaction, the phenol conversion at the outlet port of the third reactor column was 14.0%, but after 500 hours, it was 11.2%.

COMPARATIVE EXAMPLE 3

In the same reactor unit as in Example 1, acetone having a methanol concentration of 5,000 ppm was reacted with phenol in the same manner as in Example 1. In the initial stage of reaction, the phenol conversion at the outlet port of the third reactor column was 14.0%, but after 500 hours, it was 11.8%.

INDUSTRIAL APPLICABILITY

In the process of the present invention for producing a bisphenol A by continuously feeding phenol and acetone into a reactor unit having at least two reaction zones connected in series, an acidic cation-exchange resin partially neutralized with a sulfur-containing nitrogen compound in from 15 to 50 of the acid site thereof is used as the catalyst, and acetone having a methanol concentration of at most 3,000 ppm is separately fed into at least two reaction zones in the reactor unit. The advantage of the process of producing bisphenol A is that the life of the acidic cation-exchange resin catalyst used is prolonged.

What is claimed is:

1. A process for producing a bisphenol A by continuously feeding phenol and acetone into a reactor unit having at least two reaction zones connected in series, which is characterized in that an acidic cation-exchange resin partially neutralized with a sulfur-containing nitrogen compound in from 15 to 50% of the acid site thereof is used as the catalyst, and acetone having a methanol concentration of from 1,000 to 3,000 ppm is separately fed into at least two reaction zones in the reactor unit.

2. The process for producing bisphenol A as claimed in claim 1, wherein the ratio (by mol) of phenol/all acetone falls between 6 and 13.

3. The process for producing bisphenol A as claimed in claim 1, wherein the sulfur-containing nitrogen compound is at least one selected from pyridinealkanethiols, pyridylalkanethioacetals, aminoalkanethiols and thiazolidines.

4. The process for producing bisphenol A as claimed in claim 1, wherein the reaction temperature falls between 60 and 100° C.

5. The process for producing bisphenol A as claimed in claim 1, wherein from 30 to 50% of all acetone to be fed into the reactor unit is fed into the first reaction zone.

6. The process for producing bisphenol A as claimed in claim 1, wherein the liquid hourly space velocity (LHSV) in each reaction zone falls between 0.2 and 30 $hr^{-1}$.

7. The process for producing bisphenol A as claimed in claim 1, wherein the acidic cation-exchange resin catalyst is a sulfonic acid cation-exchange resin.

8. The process for producing bisphenol A as claimed in claim 1, wherein the acidic cation-exchange resin is selected from the group consisting of a sulfonated styrene-divinylbenzene copolymer, a sulfonated crosslinked styrene polymer, a phenol-formaldehyde-sulfonic acid resin, a benzene-formaldehyde-sulfonic acid resin, and mixtures thereof.

9. The process as claimed in claim 1, wherein the acidic cation-exchange resin is partially neutralized with a sulfur-containing nitrogen compound in from 20 to 50% of the acid sites.

10. The process for producing bisphenol A as claimed in claim 1, wherein the sulfur-containing nitrogen compound is 2,2-diniethylthia zolidine.

11. A process for producing bisphenol A, comprising:

continuously feeding phenol and acetone into a reactor unit having at least two reaction zones connected in series, and reacting the acetone and the phenol in the presence of an acidic cation-exchange resin, wherein the cation-exchange resin is partially neutralized with a sulfur-containing nitrogen compound present in from 15 to 50% of the acid sites of the cation-exchange resin, and acetone having a methanol concentration of from 1,000 to 3,000 ppm is separately fed into at least two reaction zones in the reactor unit.

12. The process as claimed in claim 11, wherein the molar ratio of phenol:(all acetone) is from 6 to 13.

13. The process as claimed in claim 11, wherein the sulfur-containing nitrogen compound is at least one selected from the group consisting of a pyridinealkanethiol, a pyridylalkane thioacetal, an aminoalkanethiol and a thiazolidine.

14. The process as claimed in claim 11, wherein the reacting is carried out at a temperature of from 60 to 100° C.

15. The process as claimed in claim 11, wherein from 30 to 50% f the total amount of acetone fed into the reactor unit is fed into a first reaction zone.

16. The process as claimed in claim 11, wherein the liquid hourly space velocity in each reaction zone is from 0.2 to 30 $hr^{-1}$.

17. The process as claimed in claim 11, wherein the acidic cation-exchange resin catalyst is a sulfonic acid cation-exchange resin.

18. The process as claimed in claim 11, wherein the acidic cation-exchange resin is selected from the group consisting of a sulfonated styrene-divinylbenzene copolymer, a sulfonated crosslinked styrene polymer, a phenol-formaldehyde-sulfonic acid resin, a benzene-formaldehyde-sulfonic acid resin, and mixtures thereof.

19. The process as claimed in claim 11, wherein the acid cation-exchange resin is partially neutralized with a sulfur-containing nitrogen compound in from 20 to 50% of the acid sites.

20. The process as claimed in claim 11, wherein the sulfur-containing nitrogen compound is 2,2-dimethylthiazolidine.

* * * * *